United States Patent [19]

Krovak et al.

[11] Patent Number: 4,684,614
[45] Date of Patent: Aug. 4, 1987

[54] MIXING OR PUMPING APPARATUS FOR THE TREATMENT OF FLOWABLE THIN OR HIGHLY VISCOUS MEDIA

[75] Inventors: Premysl Krovak; Miroslav Salvet, both of Prague, Czechoslovakia

[73] Assignee: Ceskoslovenska akademie ved, Prague, Czechoslovakia

[21] Appl. No.: 816,684

[22] Filed: Jan. 3, 1986

Related U.S. Application Data

[63] Continuation of Ser. No. 406,952, Aug. 10, 1982, abandoned.

[30] Foreign Application Priority Data

Aug. 10, 1981 [CS] Czechoslovakia ............... 6013-81

[51] Int. Cl.$^4$ ................ C12M 1/02; B01F 5/12; B01F 23/90
[52] U.S. Cl. .................. 435/316; 366/265; 366/305; 422/225; 422/227
[58] Field of Search ............... 435/311, 316, 289, 290, 435/813; 422/227, 225; 366/262, 263, 265, 305

[56] References Cited

U.S. PATENT DOCUMENTS

| 59,282 | 10/1866 | Shannon | 366/265 |
| 444,345 | 1/1891 | Gabbett | 366/265 |
| 611,470 | 9/1898 | Gatewood | 366/262 |
| 754,663 | 2/1955 | Duckworth | 422/263 |
| 2,390,579 | 12/1945 | Fritzberg | 366/263 |
| 3,131,212 | 4/1964 | Biller | 422/225 |

FOREIGN PATENT DOCUMENTS 7544663  4/1964  United Kingdom ............... 366/263

Primary Examiner—Sam Rosen
Assistant Examiner—William J. Herald

[57] ABSTRACT

Arrangement for the treatment of fluent, thin and highly viscous media, particularly for the fermentation of micro organisms, for mixing, pumping and the dissipation of the medium. The arrangement is based on a novel principle of bladeless mixing and pumping of fluent media of any kind and density. The main part of the arrangement is a hollow rotor with a bottom with at least a single inlet opening in the bottom. The rotor is rotated at a speed at which the treated medium due to centrifugal forces proceeds from one end of the rotor to the other one. The medium is discharged from the rotor through one or more outlet openings in the sides or in the top of the rotor; the medium is either only raised, or is also dissipated below or above the level of the fluent medium.

5 Claims, 8 Drawing Figures

MIXING OR PUMPING APPARATUS FOR THE TREATMENT OF FLOWABLE THIN OR HIGHLY VISCOUS MEDIA

This application is a continuation Ser. No. 406,952, filed Aug. 10, 1982, now abandoned.

The invention relates to an apparatus for the treatment of flowable thin and highly viscous media, particularly for the fermentation of microorganisms.

By "treatment of flowable (fluid) media" is particularly meant their mixing (homogenization), lifting (pumping), spraying or atomizing into a gaseous phase (diffusion, extraction, drying or fermentation of microorganisms, for instance by submersion).

The apparatus according to this invention is capable of performing these functions individually, or it can be adjusted so as to perform several of these functions simultaneously (for instance in the case of arrangements for fermentation).

With the arrangement according to this invention particularly, the following media can be treated by this method: newtonian and non-newtonian liquids, loose solid material and gases in combination with a liquid phase or media containing a solid, for instance fibrous particles and the like.

Arrangements for mixing liquid media are known and are divided as to the consistency of these media to mixing of newtonian and non-newtonian liquids (gels and pastes).

The mixing of a liquid or of solid loose materials with a gas (diffusion, fluidization) or dispersion or emulsification of different liquid phases equally belong to the above-mentioned processes.

According to the required results, different mixing devices are used.

Substantially two types of mixing devices are distinguished by their use with high or low speed agitators. High speed agitators are utilized for low viscous media and produce a good dispersion. However, they cannot be used with liquids of high viscosity. Solely low speed agitators can be used for the last mentioned materials, for instance, anchor agitators, band, comb agitators and the like. None of them, however, secures a perfect dispersion due to the slow stirring.

Neither of the above types of agitators, however, is suitable for fermentation, where the density of the medium changes in the course of the process.

Optimum conditions required for a perfect fermentation cannot therefore be obtained by currently used agitators. This is the case, for instance, when manufacturing yeast, antibiotics, alkaloids, polysaccharides and the like, where it is necessary to stir the medium and mix liquid, gaseous and solid phases, where the fermentation medium at the start of fermentation is usually of thin consistency and at the end has frequently the character of a pudding gel.

Similar cases are chemical reactions, for instance polymerizations, where a liquid medium at the end of polymerization is already highly viscous and a further mixing by currently used agitators would not be effective.

Some of these drawbacks of the known mixing and pumping systems are eliminated by the arrangement for treatment of flowable low and high viscous media, particularly for the fermentation of microorganisms according to this invention. This arrangement comprises a hollow rotor formed by a mantle and a bottom driven by a driving unit, whereby the bottom of the rotor is provided with at least one opening for supplying the medium from a container and the rotor is driven at such a speed that the treated medium proceeds from one end of the rotor to the other one. The bottom is of annular shape with either one central inlet opening or with a number of inlet openings beyond the circumferential part of the bottom, which are advantageously disposed symmetrically around the center of the bottom. The hollow rotor is either completely open at the top and without a cover, or is provided with a cover, whereby in the cover in the mantle and possibly also in the bottom, a number of further outlet openings are provided. The outlet and also the inlet openings can be of various shapes and can be provided with diffusors, nozzles, stream rectifiers, extensions for defoaming or for the foaming of the media, or can be provided with other extensions rectifying the stream, or for varying the amount and shape of the inlet or outlet of the medium by way of these openings.

One of the alternatives of the arrangement, which is particularly suitable for the lifting and pumping of flowable media, has a bottom and a cover of the rotor of annular shape with a single central opening for inlet and outlet of the fluid medium into and out of the rotor, these openings being provided with diffusors for rectifying the stream of the medium entering and leaving the rotor.

Another alternative of the arrangement according to this invention is designed for mixing, and produces a mutual dispersion and perfect mixing. For instance, when used for polymerization a higher conversion and increase of molecular weight of the polymer can be achieved. The mechanical mixing device operates to a certain extent like a pump, in the case given like a centrifugal pump; with some systems of treatment of flowing media these functions merge and combine with a higher efficiency.

The arrangement according to this invention can be applied either as an independent mixing device operating solely below the level of the medium and also as an independent pump for lifting any kind of fluent media, particularly of highly viscous media, and in a number of cases replaces current types of centrifugal vane pumps and the like, which are complicated in constructions and have a low energy efficiency and high hydromechanical losses.

On the other hand, when the arrangement is to perform the function of a mixing device, the lower part of the rotor has to be submerged completely or partly at its lower end in the treated fluent medium.

It is advantageous to provide within the mixing container baffles or other built-in means in the space below and/or above the level of the medium in order to provide within the mixing container both in the lower fluid part, i.e. below the level and in the upper part above the level such a whirling and dispersion of the medium, which would secure a perfect dispersion and diffusion of all components. The shaft of the hollow rotor is mounted on the main frame, on the mixing container, or on the stationary case of the hollow rotor. A part of the stationary case of the hollow rotor can also constitute baffles, a suction basket, or some other built-in elements.

Another alternative of utilization of the arrangement according to this invention adapted solely for lifting a liquid and dispersion or pumping has the lower part of the hollow rotor, which has to be submerged into the medium, surrounded by a stationary covering with a conduit for the supply of the medium to the bottom of the hollow rotor. This covering can be fixed to the main frame of the arrangement, to the mixing container, or can be part of a stationary casing housing the hollow rotor.

In the case in which no buffers or other built-in elements need be in the mixing container, on the main frame, or in the stationary case of the hollow rotor, and no central vortex is generated in the container, the medium below the level is not mixed but is solely sucked-on by way of the conduit for the supply of the medium to the bottom of the rotor which conduit is fixed to the stationary covering.

The arrangement for the treatment of fluent, particularly of viscous, media according to this invention is based on two principles, namely (1) on a vaneless mixing, and (2) on a vaneless pumping of any kind of fluent media. This arrangement permits the simultaneous treatment and working of these media in different ways, for instance, to homogenize and simultaneously pump the medium upwards, and to disperse it in fan shape into a gaseous medium, or to lift loose material with simultaneous drying or cooling by dispersion or by fluid techniques, for example.

The described hollow rotor can be the main element of a number of constructional alternatives, the constructional principles of which are known per se, and which in combination with the arrangement permit the working of fluent media of all kinds in different ways for different technical purposes and branch lines.

Two main applications of this rotor are possible, according to which part of the hollow rotor is in contact with the fluent medium.

In the first case the fluent medium enters a rotating cylindrical rotor through an inlet opening in the bottom of the rotor, for instance, by way of a tangential diffusor, the fluent medium being also removed by way of a similar diffusor through an outlet opening at the center of a cover. In this case the medium, for instance an acid, is solely in contact with the internal wall of the cylindrical mantle of the rotor, so that the main function of the rotor is pumping. The acid, entering the bottom of the rotor, is lifted by centrifugal force, namely along a rising spiral up to the cover of the rotor, from which it is removed, for instance, by a tangential diffusor. The external walls of the mantle or of the bottom of the rotor are in this case not in contact with the medium, but are in contact solely, for instance, with the external atmosphere.

In the second case the mentioned hollow rotor comes in contact with the medium at both walls of the mantle, and possibly also of the cover of the rotor. In that case, the internal walls of the mantle, of the bottom and possibly also of the cover function as a pump as in the first case, and the external wall of these parts of the rotor, where friction is generated against the medium outside the rotor, function as a mixing device. In that case the hollow rotor has to be immersed at least partially in the fluent medium, i.e. it is necessary that the bottom with the inlet opening be situated below the level of the medium in the mixing container.

The hollow rotor is either immersed completely in the medium, for instance, in a liquid, and operates in that case as do known classical mixing devices, in which the mixing is accomplished solely below the level of the liquid, or the rotor is only partially immersed, i.e. a part of the rotor protrudes above the liquid. The last mentioned case is particularly suitable for the fermentation of microorganisms, particularly in aerobic cultivating media, and furthermore for chemical reactions and diffusion of a liquid and gaseous phase, for polymerization, and for extraction and the like. In these cases, all three main functions of the arrangement according to this invention are utilized (pumping, mixing, dispersion).

Other mixing effects can arise if the cross section of the hollow rotor is not circular, but is square, ellipsoidal, or triangular, or if the mantle of the rotor is, for instance, made of corrugated sheet, forming alternate undulating extensions. In that case, edges or extensions of its mantle can act as external or internal vanes of a mixing device completely or partly immersed in the fluid medium. In the part above the liquid, i.e. in the gaseous space, for instance in air, these elements may have the function of a blower, a forced draught fan, or a defoamer in biochemical processes and the like. The hollow rotor can also have, for instance, several profiles, for instance in the immersed part a circular profile, and in the part above the liquid a rectangular or a similar profile, and vice versa.

Outlet openings, for instance in the mantle of the rotor operating as a mixing device, can be arranged in different manners for instance in several rows one below the other and the like.

The character of dispersion (fan shaped, crosswise, of the shape of a rising helix, etc.) can be changed by the shape and location of outlet openings.

The speed and amount of liquid leaving the rotor can be adjusted in dependence on the speed of rotation of the rotor, on the diameter and height of the rotor, on the size of the outlet openings, and furthermore on the distance of the inlet openings or of the inlet opening from the level of the fermentation medium in the fermenter.

In the gaseous space, where the fluid medium is present in the shape of tiny drops, mist or a thin film layer, an intensive contact of the fluid and solid phase takes place without regard to the character of the fluid inside the fermenter and thus a maximum growth of cultivated microorganisms, which are thus maximally reproduced in the space below the level.

The intensity of the processes in both cases can be influenced particularly by the speed of the rotor, by its size, by the size of inlet and outlet openings, and by the degree of immersion of the rotor below the level.

The fermenter according to this invention can be also provided with commonly used appliances, for instances with another stirring device (a propeller and the like), a defoaming device, a temperature regulator, a thermometer, an analyzer of the medium, for instance a pH meter, a sampling probe, dosing means of nutrients, of $O_2$, $CO_2$ and the like.

A mechanical foam breaker can be also installed on the rotor, for instance in the form of bars passing through the walls of the mantle below the cover of the rotor or an extended cover, extending from the rotor into the gaseous space of the mixing container above the liquid.

The arrangement according to this invention permits a perfect recirculation of the fluid medium in the fermenter without regard to its viscosity, secures a large contact surface of the fluid and gas even with highly viscous liquids, permits a dissipation of this medium into the space above the fermentation liquid (into the gaseous phase), and automatically limits foaming in the space above the fluid phase up to the height of dissipation. Another advantage is that it secures floating of a solid phase even in highly viscous media due to the suction effect of the inlet opening of the rotor.

The drive of the rotor can be provided from below or from the top, i.e. from the bottom or from the cover of the fermenter.

The fermenter according to this invention provides substantial savings in energy as compared to actually used fermenters (savings up to 30%).

An advantage of the invention is furthermore that in comparison with actually known types of fermenters where the cells of microorganisms have grown solely in the mixed lower fluid phase, the growth medium in the arrangement according to this invention passes subsequently through three working spaces which fill without residium the whole volume of the fermentation container, thus securing a large contact surface.

The fermentation arrangement according to this invention enables a perfect diffusion of a gaseous phase (for instance of $O_2$) even into media which are already of a gel or pudding character, but which are still flowing in a gravitation field.

Thus a perfect oxidizing of growing cells of microorganisms is enabled (bacteria, yeast, sponges, algae and similar). A consequence thereof is a shorter fermentation time and the achievement of a higher density of the final product in comparison with actually known types of similar arrangements.

An advantage is also the possibility of an easy regulation of the fermentation conditions at different phases of fermentation, and a smooth mixing of microorganism cells (for instance in the manufacture of antibiotics) as no considerable damage of these cells takes place, as for instance when blade or turbine agitators installed in fermentation tanks are used.

If there is solely required the pumping function of the arrangement (the first case mentioned above) it is advantageous that the bottom and the cover have an annular shape with a central opening for the supply and removal of the fluid medium into and from the rotor, whereby these openings are provided with diffusors for rectifying the stream of the medium entering and leaving the rotor.

The hollow rotor of the bladeless pump, having usually the shape of a low or high hollow cylinder with a vertical rotation axis and a horizontal bottom, is substantially a rotating vessel with openings. The shape of this vessel can be again optional (rotation cone, cylinder, polyhedron and the lime) similarly as the direction of the axis of rotation is optional (vertical, inclined, horizontal).

The rotor has here a function similar to that of the blade wheel impeller of known centrifugal pumps, i.e. its task is to transmit kinetic energy to the pumped medium; its function, however, is based on another hydrodynamic principle, different from the hydrodynamic effect of blades of the impeller wheel enclosed in a stationary case of the pump.

Whereas the blade wheel is open on its circumference and the kinetic energy is dissipated by friction on the stable internal wall of the pump case, by turbulence along the blades, and also by slip of the fluid in the gap between the case wall and the blades, the rotor according to this invention has none of these drawbacks.

The fluid medium, for instance the liquid which enters with zero angular speed into the bottom of the hollow rotor achieves in the arrangement according to this invention due to centrifugal force the shape of a rotating liquid annulus (of a liquid paraboloid), the height of which corresponds to the height of the rotor, which liquid annulus has been already created due to centrifugal forces by the liquid which has entered earlier into the bottom of the rotor. It simultaneously acquires kinetic energy and angular speed corresponding to the mantle of the rotor, even if the internal walls of the mantle of the rotor are completely smooth (they, of course, can be also roughened, provided with extensions, grooves, strips and the like).

The fluid annulus represents somehow an artificial central rising vortex which has been here created up to the height of the pumped fluid. The vortex line forms here a stable rising fluid helix. Due to large centrifugal forces, particularly no losses are experienced in this vortex and no interfering hydrodynamic moments due to turbulence, friction against stable walls, unproductive whirling and the like are present. It is a natural movement. The central vortex of the shape of a fluid annulus is entirely symmetrical and regular and its stream can be taken off in the upper part of the rotor by way of an outlet diffusor, for instance into a discharge conduit of a pump and the like, whereby the losses in the outlet stationary diffusor are relatively low (about 7%).

These reasons are also the cause of the high efficiency of this bladeless pump according to this invention and the rather low consumption of electric power for driving the rotor. Only small hydrodynamic resistances which have to be overcome are observed for the creation of the fluid annulus.

Examples of practical applications of different functions of the arrangement for the treatment of fluid media according to this invention are diagrammatically shown in the attached drawings, in which.

(Contrary to the previously mentioned "pump" of FIG. 1, in the arrangement of FIG. 2 the fluid medium is not only in contact with the internal walls of the arrangement, but is in contact simultaneously with the external walls of the hollow rotor, particularly of the mantle and bottom and is entirely immersed below the level of the medium in the mixing container.)

Figure 1:
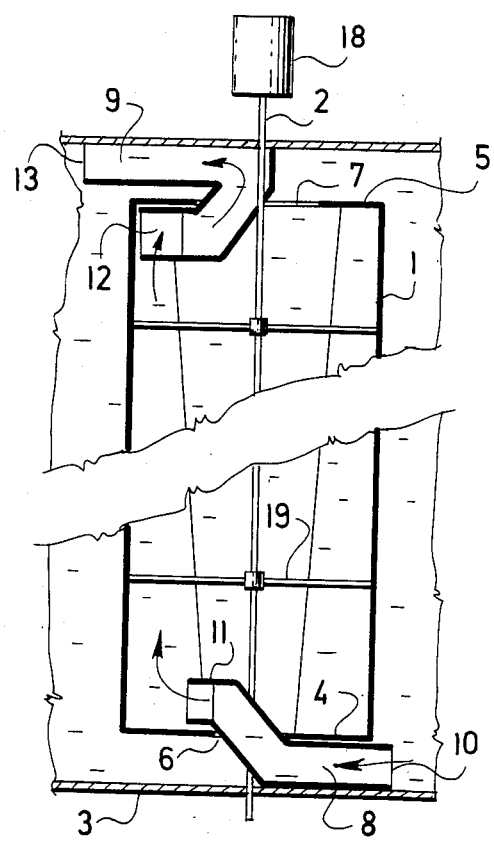
FIG. 1 is an overall sectional elevation of a first embodiment of the arrangement according to this invention, such arrangement having the function of a pump.
Figure 2:
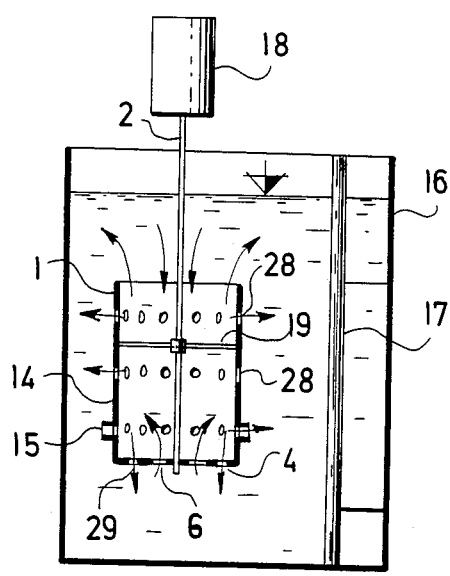
FIG. 2 is a view similar to FIG. 1 of a second arrangement according to this invention, such arrangement having the function of a classical mixing device, a disperser, an emulsifier, a homogenizer and the like which is immersed in the fluid.
Figure 4:
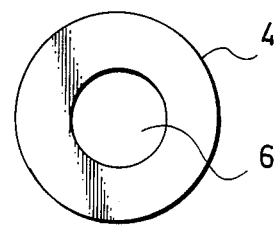
Figure 3:
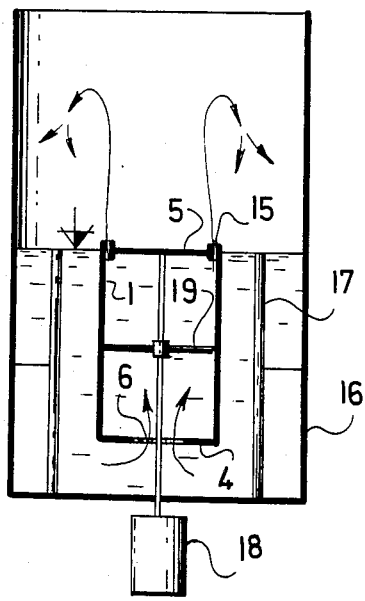
Figure 5:
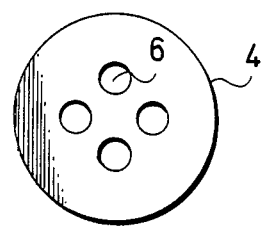
Figure 6:
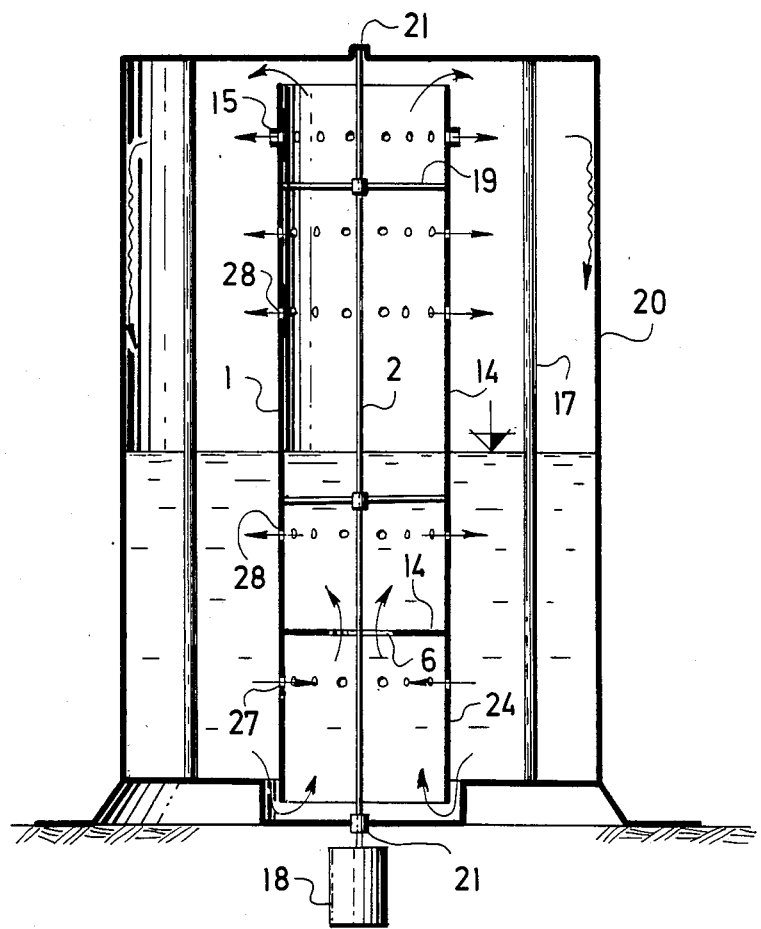
Figure 7:
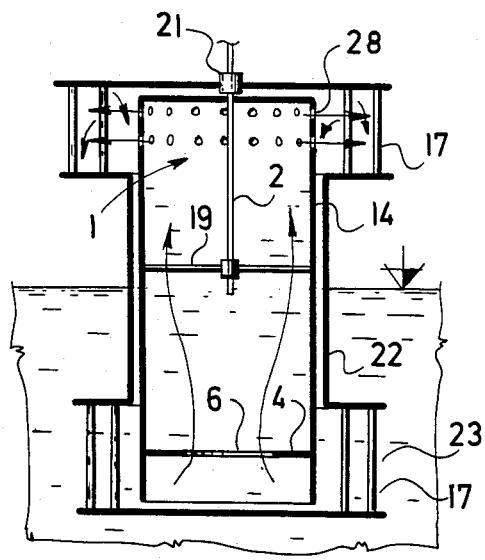
Figure 8:
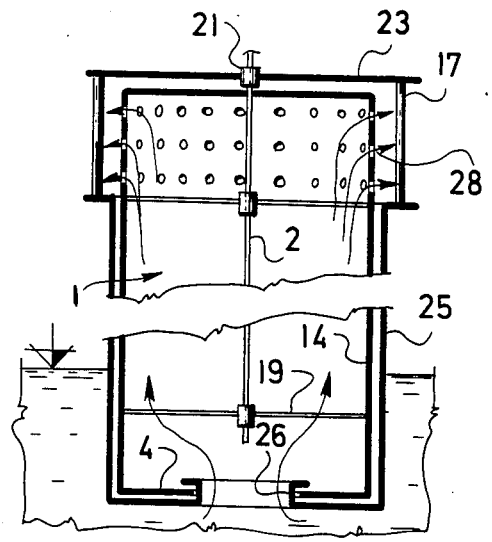

FIG. 3 is a sectional elevation of a third type of mixing device according to this invention, such arrangement mixes the fluid below the level, but disperses it simultaneously in the shape of tiny drops into the space above the fluid (where, for instance, the fluid has oxidizing properties or the like);

FIG. 4 is a top view of the bottom of the hollow rotor of annular shape with one central opening, such rotor being shown in FIG. 1;

FIG. 5 is the same view of a bottom with more inlet openings arranged symmetrically around the center beyond the circumferential part of the bottom, such rotor being shown in FIG. 2;

FIG. 6 is a diagrammatic sectional elevation of an example of a fourth arrangement, such arrangement adapted for the fermentation of microorganisms. (All the main functions of the hollow rotor are utilized in this arrangement, namely bladeless mixing, pumping and dispersion of the fluid medium;

FIG. 7 shows a fifth arrangement according to this invention, such arrangement being a portable mixing device which, contract to the arrangement shown in FIG. 6, is situated in a stationary case, parts of which are also buffers of bar shape; and with a driving unit and;

FIG. 8 shows a sixth embodiment, which is a protable pump according to this invention, situated in a stationary case the lower part of which forms a stationary cover surrounding the lower part of the hollow rotor immersed below the level of the fluid.

FIG. 1 shows a diagrammatical overall sectional elevation of an arrangement according to this invention which has the function of an independent bladeless pump.

The pump comprises a hollow rotor 1, the driving shaft 2 of which is connected with the shaft of a driving electric motor 18 which drives the rotor 1. The electric motor 18 is fixed to the main frame 3 of the pump. The rotor 1 is by means of its bearings accomodated on the frame 3, has the shape of a hollow cylinder and is connected with the shaft 2 by means of struts 19. The rotor 1 is furthermore provided at its lower end with a bottom 4 and at its upper end with a cover 5, both of which have at their center a circular opening 6 and 7, respectively, both of these parts being of annular shape.

A lower and an upper stationary tangential rectifying diffusor 8 and 9, respectively, are fixed to the lower and upper part of the frame 3. The lower diffusor 8 has an inlet 10 and an outlet 11, and the upper diffusor 9 has an inlet 12 and an outlet 13. Both rectifying diffusors 8 and 9 are formed by a rising conduit which has the shape of a loop, the diameter of which is chosen according to the required output of the pump. The loop at the lower rectifying diffusor 8 extends below the bottom 4, passes through the circular opening 6, and terminates close above the bottom 4 at an outlet 11 narrowed in fan shape.

The inlet 12 of the loop of the upper diffusor 9 is disposed close below the cover 5. This loop passes upwardly thereafter through the circular opening 7 and terminates in the outlet 13.

The pumped fluid, for instance water, is supplied through a supply conduit from the supply container outside the hollow rotor 1 and outside the frame 3 into the lower diffusor 8 with inlet 10 and enters at theoretically zero speed through the fan shaped outlet 11 tangentially at the bottom 4 of the rotor 1. In the course of a short time an annular ring (a surface paraboloid) is formed in the fluid due to rotation of the fluid within the rotor, the angular speed of rotation of the annular ring corresponding substantially to the angular rotation speed of the mantle of the rotor.

As soon as the incoming stream of water mixes with the rotating liquid annulus in the hollow rotor 1 and obtains the required energy and thus also a required centrifugal pressure, the water is raised along the internal wall of the rotor 1 and enters just below the cover through the inlet 12 into the loop of the upper diffusor 9 and leaves through the outlet 13 the upper diffusor 9.

A condition for a continuous pumping of the liquid is that the liquid must pass through both diffusors 8 and 9 in the direction of rotation of the rotor 1.

FIG. 2 shows an overall elevation of an arrangement according to this invention which has the function of a classical entirely immersed mixing device, and also the function of a pump, so that it combines both these functions.

This mixing device comprises a hollow rotor 1, the cross section of which is circular and the bottom 4 thereof is provided with four circular openings 6. The hollow rotor 1 is connected by means of struts 19 to the shaft 2, which in turn is connected to the shaft of a driving electric motor 18.

The rotor 1 has no cover; it is open at the top. Circular outlet openings 28 possibly with inserted nozzles 15 are provided in the mantle 14 of the rotor 1. The lower row of nozzles 15 has a lateral outlet opening in the opposite direction, or in the same direction as the direction of rotation of the rotor 1.

Vertical buffers 17 are furthermore arranged in the mixing container 16, which buffers are also arranged below the level of the fluid in a longitudinal direction similarly to the rotor, and are fixed to the mantle of the mixing container 16.

In this case, the hollow rotor forms two working spaces, in the mixing container 16 and in the rotor 1. The fluid is sucked into the rotor 1, and if the throughflow profile of all four openings is small with respect to the throughflow surface of the proper rotor 1 in the upper end part, the fluid also enters the rotor 1 by way of the upper open part of the rotor 1, through its center.

The fluid in the rotor 1 is raised by centrifugal force (it is pumped) along the internal walls of the mantle 14 in the form of a rising spiral and is discharged either over the rim of the rotor 1, or through outlet openings 28, 29 in the mantle 14 or in the bottom 4, or through nozzles 15 in the mantle 14 back into the fluid. The outlet openings 28, 29 the nozzles 15 or the like situated below the level of the medium contribute to a perfect mixing of the liquid phase, as they enable the injection of the medium at pressure back into the medium below the level. Simultaneously a separation of the heavier and lighter fraction of the medium can take place, so that similar fractions of different weight are present in the medium. They are again mixed after their discharge from the rotor 1. The fluid is also mixed outside the rotor 1 due to friction of the external walls of the mantle 14 of the rotor 1 with the fluid within the mixing container 16. The rotor 1 is disposed eccentrically in the container 16; an eccentric vortex is created in the container, which is, however, disintegrated by buffers 17, around which local vortex fields are generated in direction of rotation. If the cross section of the rotor 1 should have the shape of a rectangle, a triangle, a square, an ellipse or the like, then the edges, possibly also the overall shape of the rotor 1, causes a further mixing effect below the level which is similar, for instance, to that of mixing devices with blades.

FIG. 3 shows an elevation of a mixing device according to this invention which is entirely immersed in the fluid medium which is to be homogenized. Parts in FIG. 3 which are the same as those in FIG. 2 are designated by the same reference characters.

It differs from the previously described alternative (see FIG. 2) in that the cover 5 of the rotor 1 with two nozzles 15 on the circumference of the cover 5 are at the level of the medium in the mixing container 16 and no nozzles 15 or discharge openings 28, 29 are provided on the mantle 14 or bottom 4 of the rotor 1 so that the lower immersed part of the mixing device created in the medium a central dispersed vortex so that smaller local vortexes are created around the buffers 17, while the medium discharged from the interior of the rotor 1 is dissipated above the liquid by nozzles 15 in the cover 5 in the shape of a spirally rotating vortex consisting of tiny drops. In the bottom 4 there is a central circular opening 6.

The mixing device is situated at the center of the mixing container 16 and has a lower mixing system. The vertical shaft 2 of the mixing device is brought out from the mixing container 16 through its bottom and is packed in the bottom 4. The shaft 2 is connected by means of a strut 19 and the cover 5 with the hollow rotor 1. Vertical buffers 17 fixed to the mantle of the mixing container 16 prevent the creation of a central vortex in the mixing container. In a single arrangement several functions are here combined, namely, a bladeless mixing, bladeless pumping, and dispersion of the medium into a gaseous space above the level of the medium.

FIG. 4 shows a top view of a bottom 4 of annular shape with a single central inlet opening 6, and FIG. 5 shows a bottom 4 with a number of openings 6 situated symmetrically around the center of the bottom 4 beyond the circumferential part of the bottom 4. Parts in FIGS. 4 and 5 which are the same as those in FIG. 2 which are designated by the same reference characters as in the previous figures.

FIG. 6 shows an example of an arrangement for fermentation or cultivation of microorganisms in which due to growing of cells the cultivation medium becomes denser and toward the end of fermentation the originally thin liquid becomes a liquid of a honey or pudding consistency. Parts in FIG. 6 which are the same as those in FIG. 2 are designated by the same reference characters as employed in the previous figure. The arrangement comprises a fermentation container 20 with a bottom and a cover where bearings 21 of a hollow cylindrical rotor 1 with a vertical shaft 2 are provided. The part of the rotor 1 below the bottom 4 of the rotor 1 forms a suction extension 24 with an inlet opening 27.

The rotor 1 further comprises a cylindrical mantle 14, and an annular bottom 4 with a central inlet opening 6 for the inlet of the medium into the rotor 1. A number of rows of openings 28 for the outlet of the medium from the rotor 1 are provided in the mantle 14. The upper openings 28 have the shape of nozzles 15. The shaft 2 is driven by an electric motor 18 provided with a speed regulator. The shaft 2 is connected with the mantle 14 of the rotor 1 by struts 19 in the shape of a cross. Four buffers 17 of bar shape are situated inside the fermentation container 20 on its circumference. They are fixed to the bottom and cover of the fermentation container 20. The buffers 17 prevent creation of a central vortex which would be otherwise generated due to the revolving rotor 1.

The fermentation container 20 has two fundamental working spaces, the lower fluid, and the upper gaseous; a third working space is located inside the rotor 1. In the course of rotation of the cylindrical rotor 1, which is partly immersed in the liquid space, the liquid medium enters through the central opening 6 in the bottom 4 into the rotor 1. The liquid medium is raised in the rotor 1 due to centrifugal forces along a rising spiral, and is dissipated in the shape of tiny drops through outlet openings 28 in the mantle 14 or through nozzles 15 from the rotor 1 back into the fermentation container 20 into its upper gaseous working space. Due to striking against a solid buffer 17 inside the container 20 or against the internal wall of the fermentation container 20, the drops are dissipated, whereafter the liquid flows in the shape of thin film down along the walls of the fermentation container 20 and reunites with the liquid in the lower liquid space of the fermentation container 20 at its level.

An intensive diffusion of gas into the liquid medium takes place in the gaseous working space, for instance an intensive oxidation of growing cells of microorganisms which are fermented in the fermentation container 20. A perfect mixing of the cultivation medium also takes place in the liquid space due to rotation of the lower part of the rotor 1 which is immersed in the liquid.

With a certain adjustment of nozzles 15 or of outlet openings 28 in the mantle 14, and with a suitable angular speed of the rotor 1, the required centrifugal pressure is generated in the liquid within the rotor 1, so that the discharge of the liquid medium at this pressure can be utilized above the level, for instance for breaking down the created foam above the liquid in the course of fermentation; this contributes to an increase of efficiency of fermentation and also to a reduction of energy demands and a simplification of the whole arrangement, so that no application of a defoaming liquid or an installation of a mechanical defoaming device requiring the expenditure of substantial energy is required.

The fermentation container 20 has a particular shape of its bottom. A recess is provided in the bottom into which the lower part of the hollow rotor 1 engages which lower part forms a lower extension 24 of the rotor 1. The extension 24 secures a better suction of the fluid medium from the bottom of the fermentation container 20.

The arrangement for fermentation according to this invention can be applied for the fermentation of all kinds of media, namely low viscous media, high viscous media, and also those which in the course of fermentation change their viscosity or form a suspension with lumpy or fibrous products, and also of all liquids of the non-newtonian type.

FIG. 7 shows diagrammatically a portable mixing device situated in a stationary housing or casing 23. Parts in FIG. 7 which are the same as those in FIG. 2 are designated by the same reference characters as those employed in the previous figure. Buffers 17 are provided in the mantle of the casing 23 in the lower part of the casing 23 for the generation of local vortexes and turbulences in the liquid part of the mixed medium and in the upper part of the casing 23 for the dissipation of the medium flowing from the outlet openings 28 in the space above the level to tiny drops. The buffers 17 in the upper and lower part of the casing 23 are connected by columns 22.

The lower part of the hollow rotor 1 is immersed in the liquid in the mixing container 23; the upper part extends beyond the liquid. The upper edge of the rotor 1 is closed by a cover 5. The shaft 2 is fixed to the cover 5 of the rotor 1 and is also connected with the mantle 14 of the rotor 1 by a strut 19.

This mixing device operates in a manner similar to the arrangement according to FIG. 6; the buffers 17 (the built-in part) and a driving unit is however part of the casing 23 of the rotor 1 and not part of the mixing container 23.

The arrangement is also suitable, in a manner similar to that of the earlier described arrangement, for polymerization and for other chemical reactions of thin and highly viscous media, for the treatment of sludge and industrial waste waters, and the like.

In FIG. 8 the same reference characters for parts which are similar to those in FIG. 2 are designated by the same reference characters as those employed in connection with FIG. 2.

FIG. 8 shows an arrangement of a bladeless pump which dissipates the raised medium laterally; this arrangement is situated in a stationary casing 23, the lower part of which casing forms a stationary shield 25 partially surrounding the lower part of the hollow rotor 1 immersed below the level. This thus prevents contact of the external walls of the mantle 14 and of the bottom 4 of the rotating hollow rotor 1 with the fluid medium below its level. Buffers 17 are provided solely in the upper part of casing 23. In the mantle 14 there are outlet springs 28.

The shield 25 below the level of the medium has a function similar to that of buffers 17 or some other built-in part in the space below the level of the medium, since it prevents the creation of a central vortex within the fluid medium. In this case, the medium in the lower part is not fixed due to contact of the external walls of the mantle 14 with the medium, and the rotor 1 has above all the function of a self-sucking-on submerged pump in which the raised medium is in the respective height dissipated into the surrounding space. A suction basket can be provided in the lower part of the casing 23, its task being to filter the medium.

The arrangement according to FIG. 8 can be, for instance, applied in known fluid techniques, for cooling liquids, drying of pulverous media, watering the soil and the like.

The applications of the arrangements of the invention are universal, depending upon what kind of medium the various arrangements according to this invention are to operate, whether or not they are immersed for instance, in a liquid (as a pump), whether they are completely immersed in the liquid (an entirely immersed mixing device) or whether they are only partially immersed (for instance a fermenter for cultivation of microorganisms). The arrangements can be applied for different methods of treatment of fluid or liquid media of any consistency, particularly in chemistry, pharmacology, machinery, heat technique (heat transmitters), water cleaning plants, water plants, in the manufacture of paints and varnishes, and also in other industrial branches and in agriculture (watering, drying or foodstuff, of grain, dosing of foodstuff, of liquid fertilizers and the like).

The arrangements according to this invention can also be utilized advantageously due to their simple constructions for treatment of aggressive liquid (acids, lye) and possibly also gases. In the mentioned branches, it can be useful both in shops and in laboratories.

The arrangements can operate under any conditions, for instance, at different temperatures, pressures or in a vacuum, in an electric, magnetic or other power field, and so forth.

Another advantage is that the arrangements are of simple construction and their manufacture is less demanding on labor when compared with other arrangements. Mass production could be, for instance, secured from suitable plastics by use of injection molding press.

Although the invention is illustrated and described with reference to a plurality of embodiments thereof, it is to be expressly understood that it is in no way limited to the disclosure of such preferred embodiments but is capable of numerous modifications within the scope of the appended claims.

We claim:

1. A mixing or pumping apparatus for liquid medium, comprising:
   a container which contains a fluent medium which is to be mixed or pumped,
   a hollow cylindrical rotor with a horizontal bottom,
   said hollow cylindrical rotor being at least partly submerged under the level of the fluent medium in the container,
   said horizontal bottom being provided with a central circular inlet opening for supply of the medium from said container to the interior of said rotor, said inlet opening being concentric with the longitudinal axis of said cylindrical rotor whereby when said rotor is rotated at a sufficiently high speed a strong suction is effected at said inlet opening,
   driving means imparting to said hollow rotor a rotational movement at a speed at which due to centrifugal force the medium within the container proceeds from the lower end of the rotor to the upper end thereof and forms there a surface paraboloid and
   means in the top of the rotor for the discharge of the medium through the top of said rotor above the surface of the fluent medium.

2. An apparatus as claimed in claim 1 further comprising means for discharging the medium from the sides of the rotor.

3. An apparatus as claimed in claim 1 further comprising a stationary casing at least partly submerged in said fluent medium within said container, said casing surrounding said rotor and communicating with the fluent medium.

4. An apparatus as claimed in claim 3 wherein said casing is provided with a casing bottom, said casing bottom being provided with a casing inlet opening, said casing inlet opening communicating with a tube, said tube communicating with and terminating above said inlet opening of said rotor bottom.

5. An apparatus as claimed in claim 1 wherein said container is provided with a central circular recess in its bottom, said rotor being positioned to occupy a portion of said circular recess in a manner to permit said medium to flow into said recess and enter said central opening in the bottom of said rotor.

* * * * *